United States Patent
Howard

(10) Patent No.: US 8,394,071 B2
(45) Date of Patent: Mar. 12, 2013

(54) VENOUS LINE DISCONNECTION / VENOUS NEEDLE DISLODGEMENT CLAMP

(76) Inventor: Peter Howard, Tunstall Stoke on Trent (GB)

(*) Notice: Subject to any disclaimer, the term of this patent is extended or adjusted under 35 U.S.C. 154(b) by 472 days.

(21) Appl. No.: 12/595,714

(22) PCT Filed: Apr. 14, 2008

(86) PCT No.: PCT/GB2008/001299
§ 371 (c)(1),
(2), (4) Date: Oct. 13, 2009

(87) PCT Pub. No.: WO2008/125838
PCT Pub. Date: Oct. 23, 2008

(65) Prior Publication Data
US 2010/0056976 A1    Mar. 4, 2010

(30) Foreign Application Priority Data
Apr. 14, 2007  (GB) .................................. 0707241.6

(51) Int. Cl.
*A61M 5/00*  (2006.01)
(52) U.S. Cl. ........................................ 604/250; 604/246
(58) Field of Classification Search .......... 604/246–256, 604/174–180
See application file for complete search history.

(56) References Cited

U.S. PATENT DOCUMENTS

| 4,944,485 A | * | 7/1990 | Daoud et al. ...................... 251/9 |
| 5,338,313 A | * | 8/1994 | Mollenauer et al. .......... 604/249 |
| 6,749,591 B1 | | 6/2004 | McNally et al. |

FOREIGN PATENT DOCUMENTS

| DE | 19822214 A1 | 11/1999 |
| DE | 19951669 A1 | 4/2001 |

* cited by examiner

*Primary Examiner* — Kevin C Sirmons
*Assistant Examiner* — Phillip Gray
(74) *Attorney, Agent, or Firm* — Brooks Kushman P.C.

(57) ABSTRACT

In renal haemodialysis there is a condition whereby the patient can by at serious risk of harm if the venous line becomes disconnected or the venous needle becomes dislodged and the haemodialysis machine does not detect this condition. The invented device is designed to safeguard haemodialysis patients from serious losses of blood through venous line disconnection or venous needle dislodgement. The invented device is designed to clamp the venous line automatically before venous needle dislodgement or venous line disconnection becomes a serious problem and to make the haemodialysis machine stop drawing blood from the patient This will cause the haemodialysis machine to alarm in the normal way so as to alert the patient or healthcare worker to the problem. The invented device will have to be manually reset before therapy can continue.

11 Claims, 5 Drawing Sheets

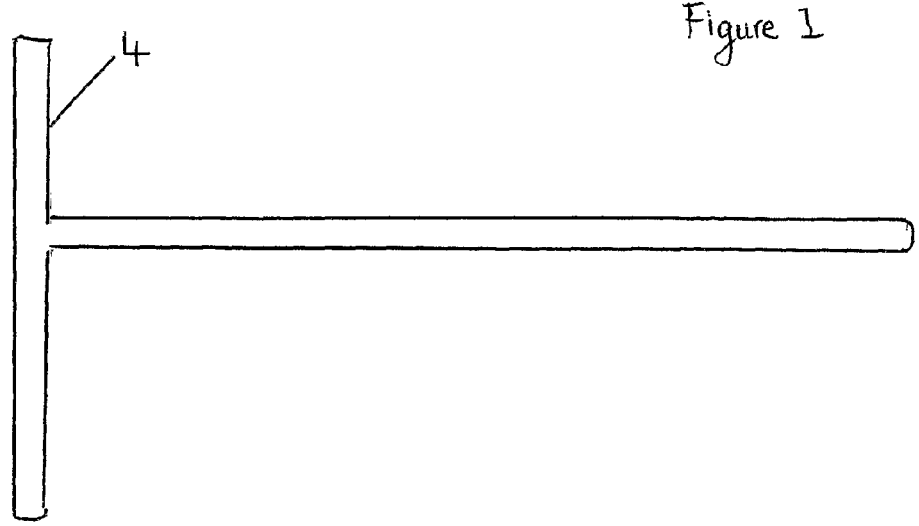
Figure 1
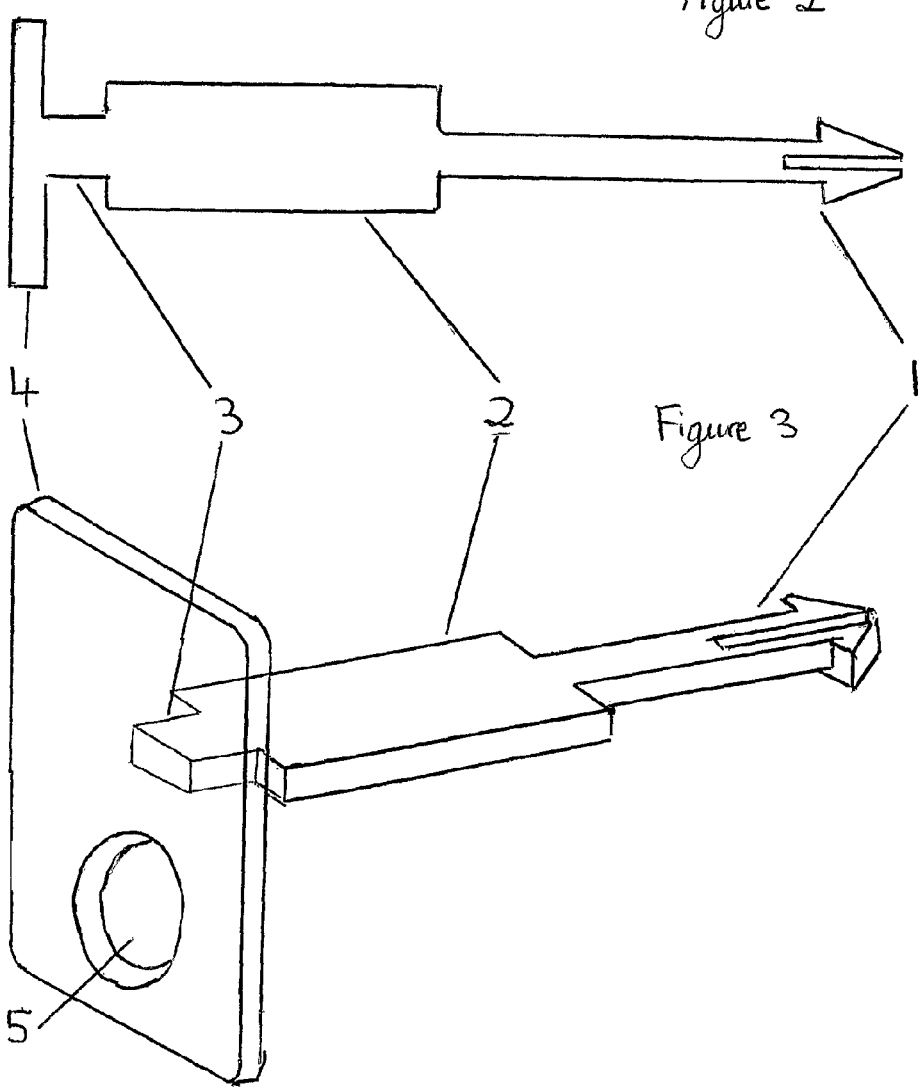
Figure 2
Figure 3

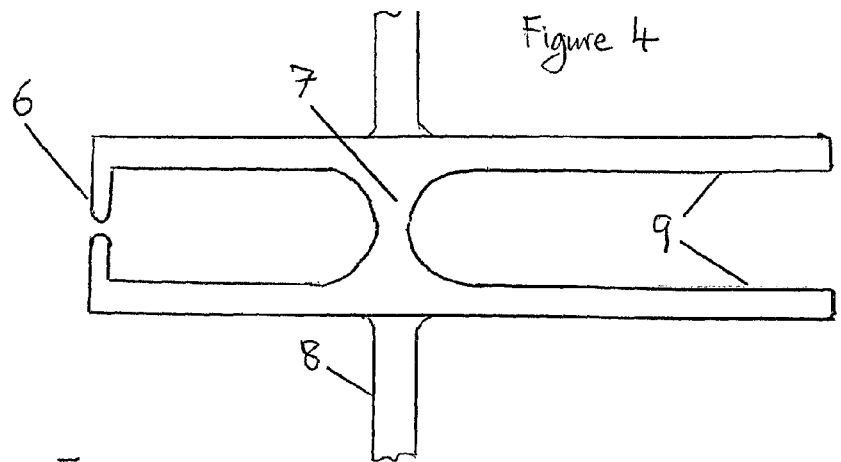
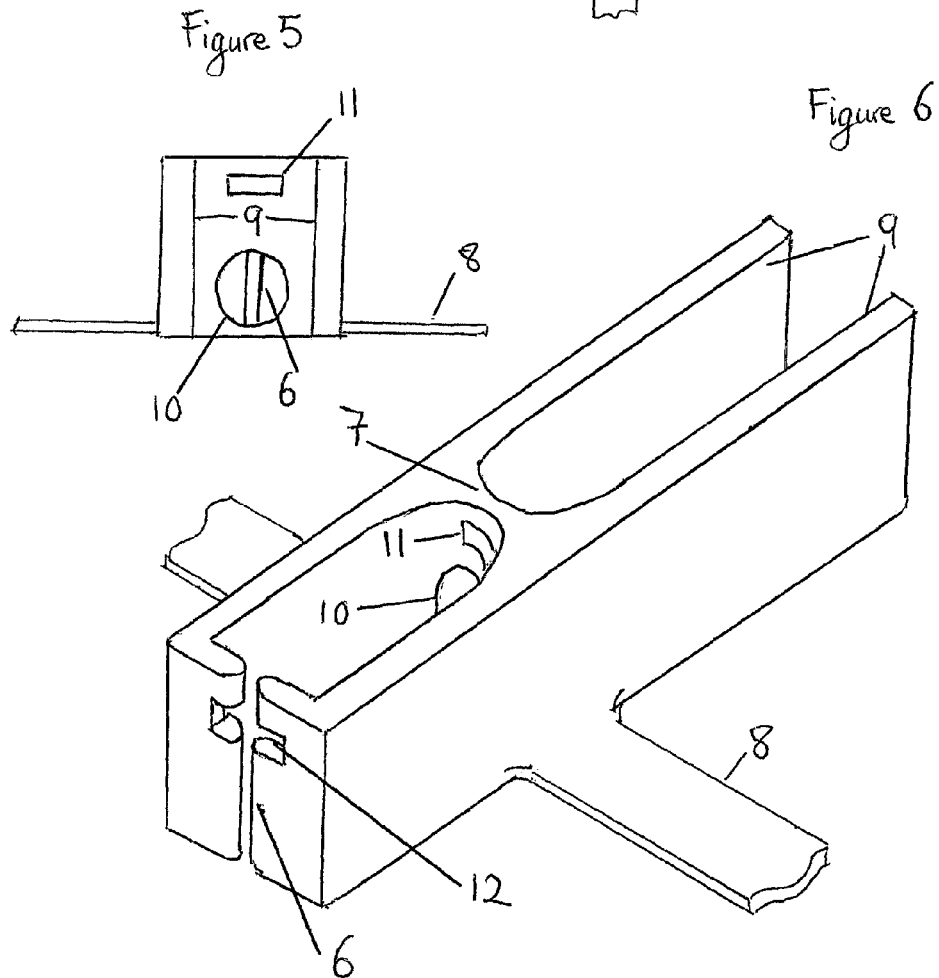

VENOUS LINE DISCONNECTION / VENOUS NEEDLE DISLODGEMENT CLAMP

This invention relates to the therapy of haemodialysis.

DESCRIPTION OF PROBLEM

During a haemodialysis therapy blood is drawn from the patient, treated by a haemodialysis machine and then returned back into the patient at blood flow rates typically of between 200 ml/min to 450 ml/min through extracorporeal tubing. The haemodialysis machine that processes the blood has various means of ensuring that the patient receives a safe as possible therapy. The blood that is travelling through the extracorporeal blood line is monitored for pressures as the blood is leaving the patient (arterial pressure), as the blood is returning back to the patient (venous pressure) and for any air that may have inadvertently entered the blood lines. Under normal circumstances the patient is treated quite safely. However, there is a condition whereby the patient is placed under danger of serious illness or death. This is when the venous line becomes disconnected or the venous needle is dislodged from the patient. In certain conditions the dialysis machines venous pressure monitoring system cannot distinguish when the venous line has become disconnected or the venous needle has dislodged from the patient. The result is that blood is continually drawn from the patient and treated but instead of returning back into the patient in a safe manner, it is allowed to flow outside of the patient via the disconnected or dislodged venous line or needle. Consequently, the patient is drained of blood within minutes if left undetected. This can easily happen if the patient is asleep and covered in a blanket.

DESCRIPTION OF SOLUTION

The function of the invented device is to automatically clamp the venous line before venous line disconnection or needle dislodgement becomes a serious health hazard to the patient. The clamping action will provide a pressure in the venous blood line which will be detected by the haemodialysis machine. The haemodialysis machine will stop the flow of the blood being drawn from the patient and alert a healthcare worker via the normal haemodialysis alarm system. The invented device will have to be manually reset before blood is allowed to pass though it for therapy purposes, thus allowing for corrective action prior to commencement of therapy.

INVENTION DETAIL SUPPORTED BY DIAGRAMS

The invented device is made up of two components; component A and component B, which when combined together make up the working device. The first component (A) is illustrated in FIGS. 1, 2 & 3.

FIG. 1 shows a side view;

FIG. 2 shows a top view and

Figure 7:
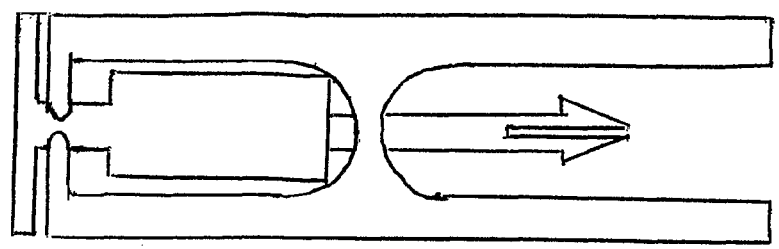

FIG. 3 shows a three dimensional view. Component A has several features and is the moveable part of the invention. Feature 1 locates and retains the component A into component B via feature 11, the guide hole. Feature 2 wedges open the clamp (feature 6). Feature 3 which is a reduction in the width of the wedge allows the clamp (feature 6) to dose squeezing the two sides of the blood line together. Feature 4 is both the plate on which force is exerted to slide the component A into component B and is also a means of returning the device back to being an open clamp by pushing back component A from component B. This is achieved by squeezing the two sides of the rear of component B together (feature 9) to open the clamp (feature 6) before pushing feature 4 back and thus manually resetting the device so that it is open. Feature 5 is an access hole for the blood tubing.

The second component (B) is illustrated in FIGS. 4, 5 & 6.

FIG. 4 shows a top view;

FIG. 5 a view from the rear (looking in the direction of blood flow towards the patient) and FIG. 6 shows a three dimensional view. As mentioned above feature 6 is the clamp; feature 9 is the clamp release and feature 11 is a guide hole. In addition feature 7 provides the spring to give the clamp adequate force to clamp the blood line; feature 10 is an access hole for the blood line; feature 12 is the wedge guide and feature 8 is to aid the fixing of component B to the patient.

Figure 8:
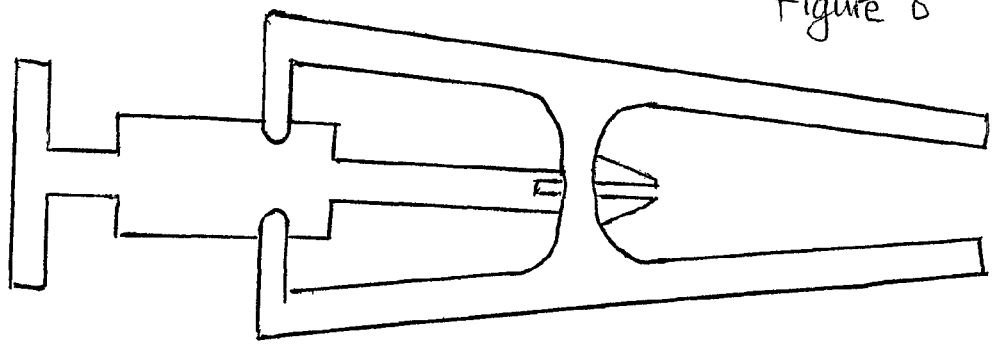

FIGS. 7 & 8 illustrate from a top view the action of the two components of the device.

FIG. 7 shows the device in a clamping position and

FIG. 8 shows the device in an open clamp position.

Figure 9:
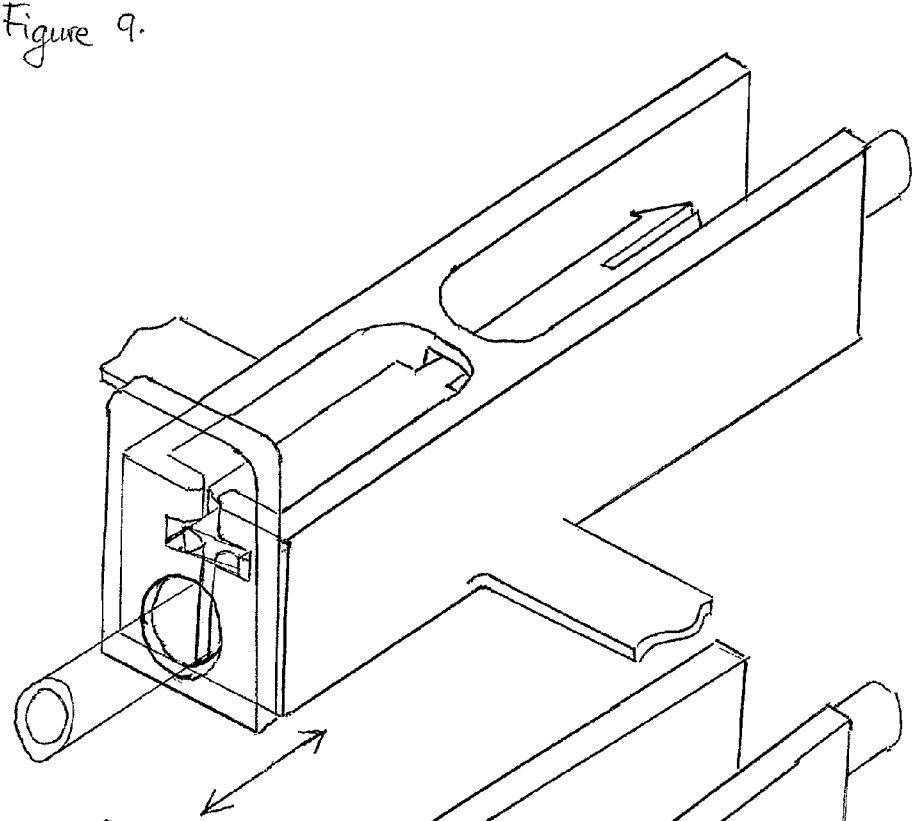
Figure 10:
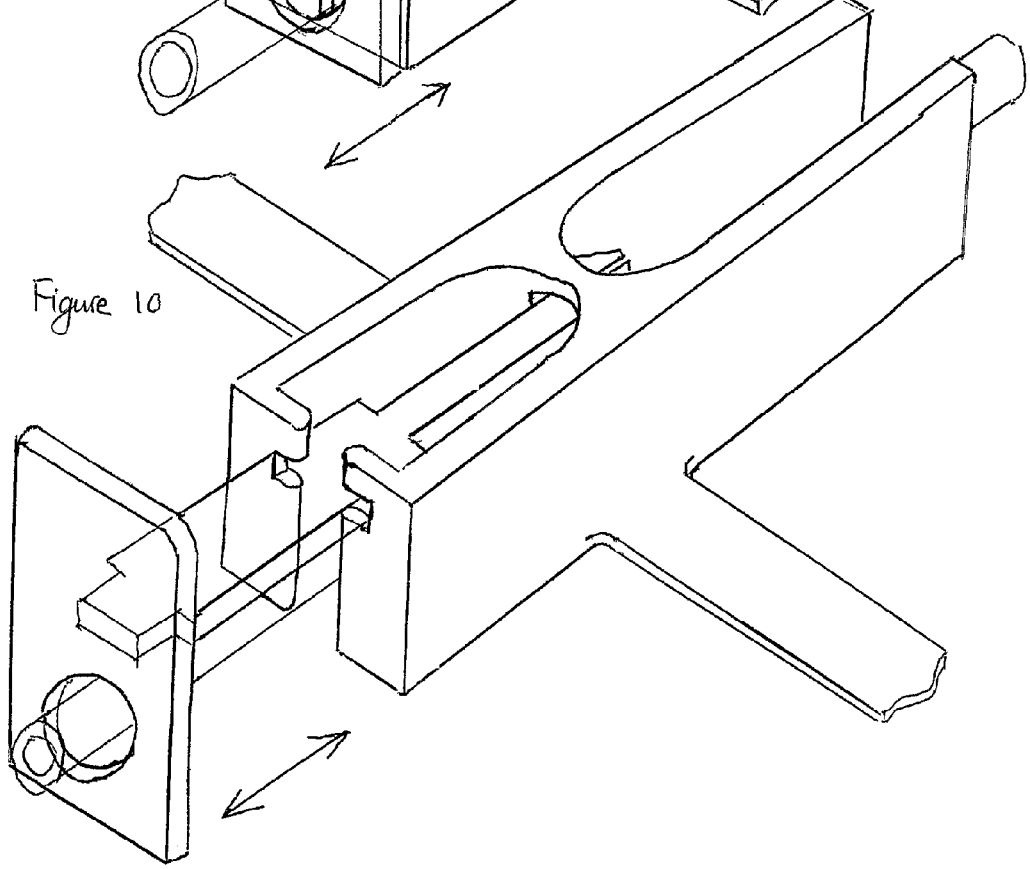

FIGS. 9 & 10 show both the clamped and the unclamped positions in a three dimensional view with component A illustrated as a 'see through' drawing to allow the detail of component B to be viewed. Also the blood tubing is illustrated to show the clamping effect.

Figure 11:
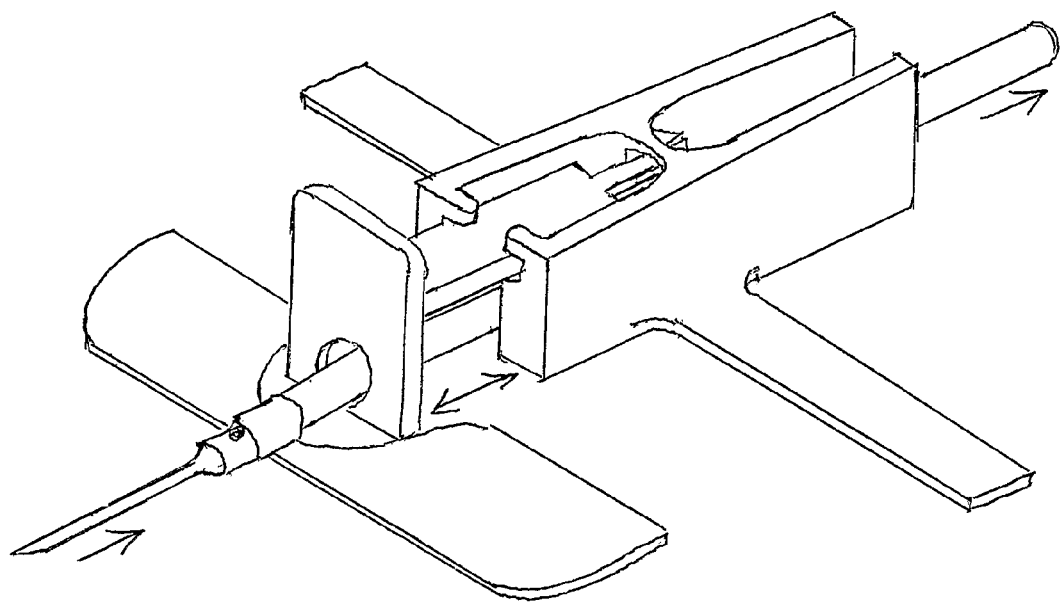
Figure 12:
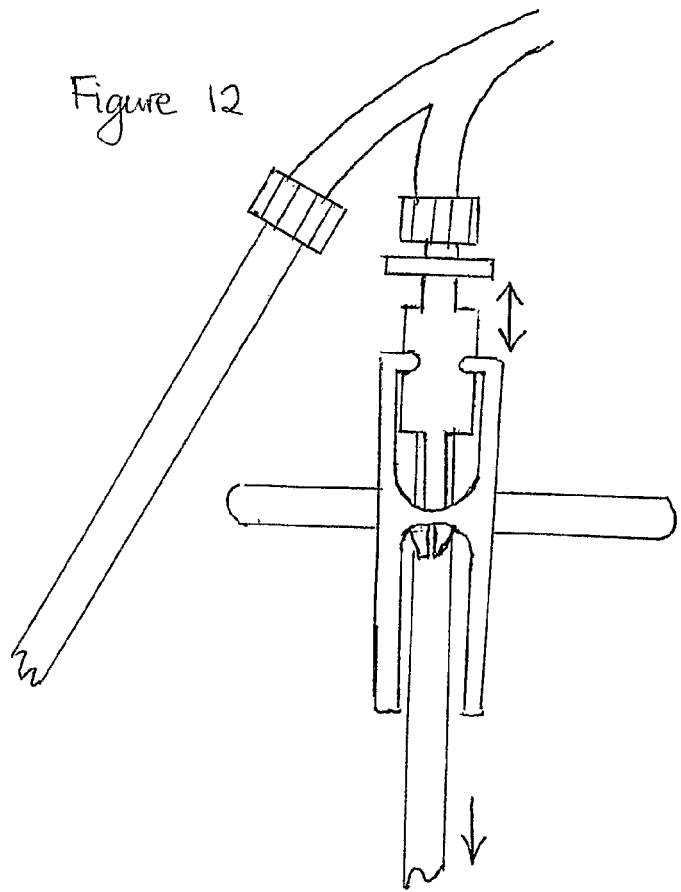

FIGS. 11 & 12 show the applications of the device.

FIG. 11 shows the correct positioning of the device with components A and B fully parted and component A sited up against the needle. If the needle were to be disturbed by a force which would start to pull it out of the patient, then component A would slide towards component B which is fixed to the patient. Eventually component A would have travelled far enough into component B for it to clamp the blood line and thus setting of the haemodialysis machines venous pressure alarm and thus stopping the blood flow before any major incident could occur.

Like wise in FIG. 12 the device is positioned in the same way, fully extended, against the joining of the venous blood line to a catheter. If the join were to become detached then the downward force of the venous line would push component A into component B and clamp the blood line in the same way making the haemodialysis machine alarm and stopping the blood flow before the occurrence of a major incident.

In both applications a manual resetting of the clamp would be necessary to allow the continuation of therapy having removed the cause of disconnection/dislodgement.

The invention claimed is:

1. A two part extracorporeal blood tubing clamp to help protect a haemodialysis patient from significant blood loss during therapy, comprising:

a movable part A, having an aperture for blood tubing, an end plate section to actuate movement of part A, a varying width wedge section to hold the clamp open and to close the clamp when actuated, a location and retention guide to locate and retain part A into part B, and a fixed part B, having a clamping section, a flexible spring like section disposed at a pivot, the flexible spring like section having a bias to a closed clamping section condition, a wedge guide recess, a wedge guide/retention hole, a blood tubing aperture, a clamp resetting/release section, and a patient fixing section, the pivot being disposed between the clamping section and the clamp resetting/release section, and so in operation when movable part A is in a fully extended position with respect to part B, the varying width wedge section holds the clamping section of the clamp open, while when the movable part A is slid towards part B the varying width wedge section allows the flexible spring like section to close the clamp thereby clamping the blood tubing with the clamping section, and the resetting/release clamp section when squeezed together allows the release of part A to its extended position by exertion on the end plate.

2. The clamp of claim 1 wherein the patient fixing section is adapted to be secured to the patient's skin or extended to fix around the patients arm or attached to a catheter attached to the patient.

3. The clamp of claim 1 wherein the activation of the clamp is configured to activate a standard alarm system on a haemodialysis machine and stop the therapy until the clamp is manually reset.

4. A two part extracorporeal blood tubing clamp to help protect a haemodialysis patient from significant blood loss during therapy, the clamp comprising:
 a movable part A having a plate transversely connected to a first end of an elongated member having an longitudinal axis, the plate having an aperture, the elongated member having a wedge along the longitudinal axis, a reduction adjacent to the plate, and a retention portion adjacent to a second end of the elongated member; and
 a fixed part B having a clamping section, a clamp release section, and a flexible section, the clamping section having at least two opposed and spaced apart elongated members, the clamping section being disposed adjacent to the first end of the elongated member, the clamping section having an aperture adjacent to and cooperating with the plate aperture, the clamping section having an open condition and a closed condition, the clamp release section having at least two opposed and spaced apart elongated members, the flexible section being disposed between the clamping section and the clamp release section and connecting the clamping section elongated members and the clamp release section elongated members forming a pivot.

5. The clamp of claim 4, wherein the reduction and the clamping section have an interference fit when in the closed condition.

6. The clamp of claim 4, wherein the wedge and the clamping section have an interference fit when in the open condition.

7. The clamp of claim 4, wherein the flexible section defines a wedge guide aperture cooperating with the elongated member along the longitudinal axis.

8. The clamp of claim 4, further comprising a flange connected to fixed part B and disposed transversely to the longitudinal axis, the flange adapted for securing the clamp to a user.

9. A two part extracorporeal blood tubing clamp to help protect a haemodialysis patient from significant blood loss during therapy, the clamp comprising:
 a part A having an elongated member having a planar wedge along a longitudinal axis, a reduction at a first end, and a retention portion adjacent to a second end; and
 a part B having a clamping section, a clamp release section, and a flexible section, the clamping section having at least two opposed and spaced apart elongated members each with a transverse flange being inwardly directed toward the longitudinal axis and being disposed adjacent to the first end of the part A elongated member and defining a aperture, the clamping section having an open condition and a closed condition, the flexible section being disposed between the clamping section and the clamp release section and connecting the clamping section elongated members and the clamp release forming a pivot.

10. The clamp of claim 9, further comprising a flange connected to fixed part B and disposed transversely to the longitudinal axis, the flange adapted for securing the clamp to a user.

11. The clamp of claim 9, wherein the retention portion includes elongated members each having a outwardly directed flanges directed away from the longitudinal axis.

\* \* \* \* \*